United States Patent
Hui

(10) Patent No.: US 9,512,392 B2
(45) Date of Patent: Dec. 6, 2016

(54) METHOD TO INCREASE DISSOLVED OXYGEN IN A CULTURE VESSEL

(75) Inventor: Mizhou Hui, Thousand Oaks, CA (US)

(73) Assignee: ZHEJIANG JINYISHENGSHI BIOENGINEERING CO., LTD, Huzhou (CN)

(*) Notice: Subject to any disclaimer, the term of this patent is extended or adjusted under 35 U.S.C. 154(b) by 1540 days.

(21) Appl. No.: 12/303,837

(22) PCT Filed: Sep. 27, 2006

(86) PCT No.: PCT/US2006/037468
§ 371 (c)(1),
(2), (4) Date: Mar. 12, 2010

(87) PCT Pub. No.: WO2007/142664
PCT Pub. Date: Dec. 13, 2007

(65) Prior Publication Data
US 2010/0190245 A1    Jul. 29, 2010

(30) Foreign Application Priority Data
Jun. 8, 2006 (WO) ................ PCT/US2006/022312

(51) Int. Cl.
*C12N 5/071* (2010.01)
*C12M 1/00* (2006.01)
*C12M 3/04* (2006.01)
*C12M 3/06* (2006.01)

(52) U.S. Cl.
CPC ............ *C12M 23/02* (2013.01); *C12M 27/12* (2013.01); *C12M 27/16* (2013.01); *C12M 27/20* (2013.01); *C12N 2500/02* (2013.01)

(58) Field of Classification Search
CPC .............................. C12M 27/16; C12M 27/20
USPC ............................................ 435/304.1, 325
See application file for complete search history.

(56) References Cited

U.S. PATENT DOCUMENTS

| 4,824,787 | A  |   | 4/1989  | Serkes          |         |
|-----------|----|---|---------|-----------------|---------|
| 4,912,048 | A  |   | 3/1990  | Smith et al.    |         |
| 5,002,890 | A  |   | 3/1991  | Morrison        |         |
| 5,270,207 | A  | * | 12/1993 | Matsumura et al.| 435/295.1 |
| 5,330,908 | A  |   | 7/1994  | Spaulding       |         |
| 5,665,594 | A  |   | 9/1997  | Schwarz         |         |
| 6,096,544 | A  | * | 8/2000  | Bramble et al.  | 435/394 |
| 6,190,913 | B1 | * | 2/2001  | Singh           | 435/394 |
| 6,391,638 | B1 |   | 5/2002  | Shaaltiel       |         |
| 6,991,933 | B1 |   | 1/2006  | Upton et al.    |         |
| 2002/0025547 | A1 |   | 2/2002 | Rao           |          |
| 2002/0110915 | A1 | * | 8/2002 | Shaaltiel     | 435/393  |
| 2005/0101009 | A1 | * | 5/2005 | Wilson et al. | 435/295.3 |
| 2005/0106045 | A1 |   | 5/2005 | Lee           |          |

FOREIGN PATENT DOCUMENTS

WO           02/42409 A1   5/2002
WO   WO 2006/138143 A    12/2006

OTHER PUBLICATIONS

De Jesus et al., TubeSpin satellites: a fast track approach for process development with animal cells using shaking technology, Biochemical Engineering Journal, vol. 17, 2004, p. 217-223.*
Wurm et al., Disposable orbital shake bioreactor system from ml to 1000 L for cell culture-from concept to reality.*
Jordan et al., A versatile disposable culture system for high throughput screening of process parameters and production cell lines, Animal Cell Technology meets Genomics, Proceeding of the 18th ESACT Meeting, 2003, p. 381-383.*
http://www.tpp.ch/page/produkte/13_zentrifugen_roehrchen.php?lang=EN TTP Centrifuge Tube for centrifugation and other applications.*
Muller, N. et al. "Orbital Shaker Technology for the Cultivation of Mammalian Cells in Suspension" Biotechnology and Bioengineering, vol. 89, No. 4, pp. 400-408 (2005).
Kato, Y. et al. "Effects of Liquid Film Formed on Flask Surface on Oxygen Transfer Rate in Shaking Flask and Development of Baffled Shaking Vessel by Optical Method Based on Sulfite Oxidation" Journal of Chemical Engineering of Japan, vol. 38, No. 11, pp. 873-877 (2005).
Singh, Vijay. "Disposable bioreactor for cell culture using wave-induced agitation" Cytotechnology, vol. 30, No. 1-3, pp. 149-158 (1999).
Mano, T. et al. "Comparison of Oxygen Supply Methods for Cultures of Sheer-Stress Sensitive Organisms Including Animal Cell Culture" Journal of Chemical Technology and Biotechnology, vol. 47, No. 3, pp. 259-271 (1990).
Varley, J. et al. "Reactor design for large scale suspension animal cell culture" Cytotechnology, vol. 29, No. 3, pp. 177-205 (1999).
Zhang, X. et al. "Shaken helical track bioreactors: Providing oxygen to high-density cultures of mammalian cells at volumes up to 1000L by surface aeration with air" New Biotechnology, vol. 25, No. 1, pp. 68-75 (2008).
European Examination Report dated Jul. 3, 2012 issued in European Patent Application No. 06815465.7.

* cited by examiner

*Primary Examiner* — Taeyoon Kim
*Assistant Examiner* — Tiffany Gough
(74) *Attorney, Agent, or Firm* — Scully Scott Murphy & Presser

(57) ABSTRACT

Basing on study of a previous discovered effective bioreactor system, a method to increase culture medium dissolved oxygen is disclosed. This method together with addition of an optimal mixing forms a theoretical foundation for effective bioreactor design and prototype construction.

6 Claims, 19 Drawing Sheets

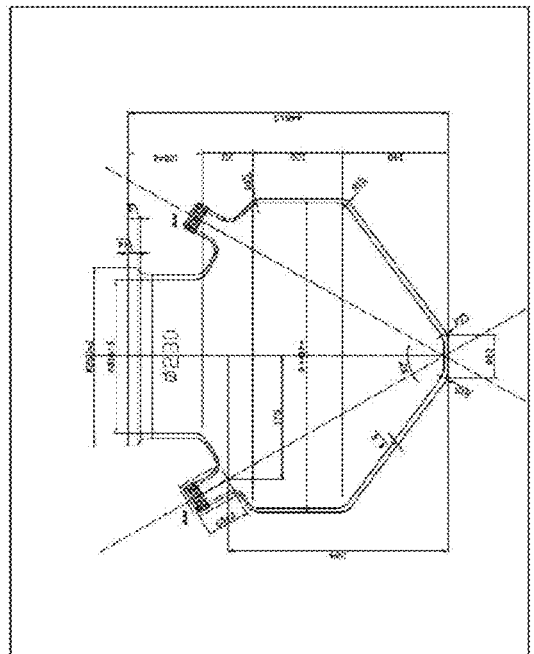
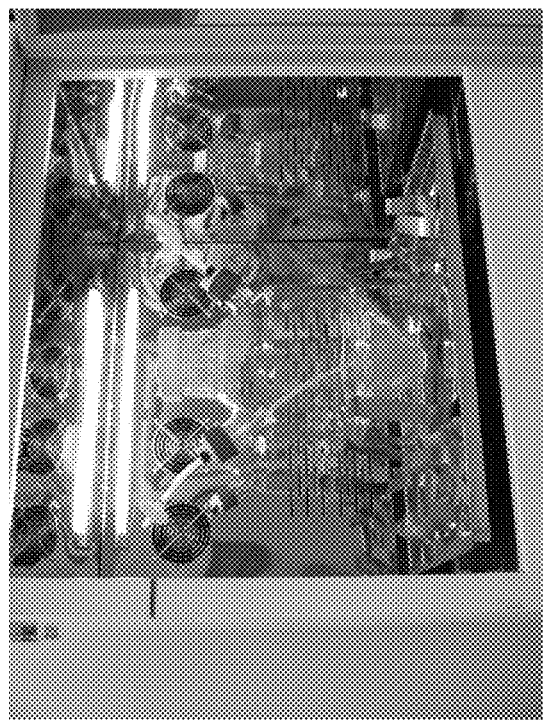
Figure 1

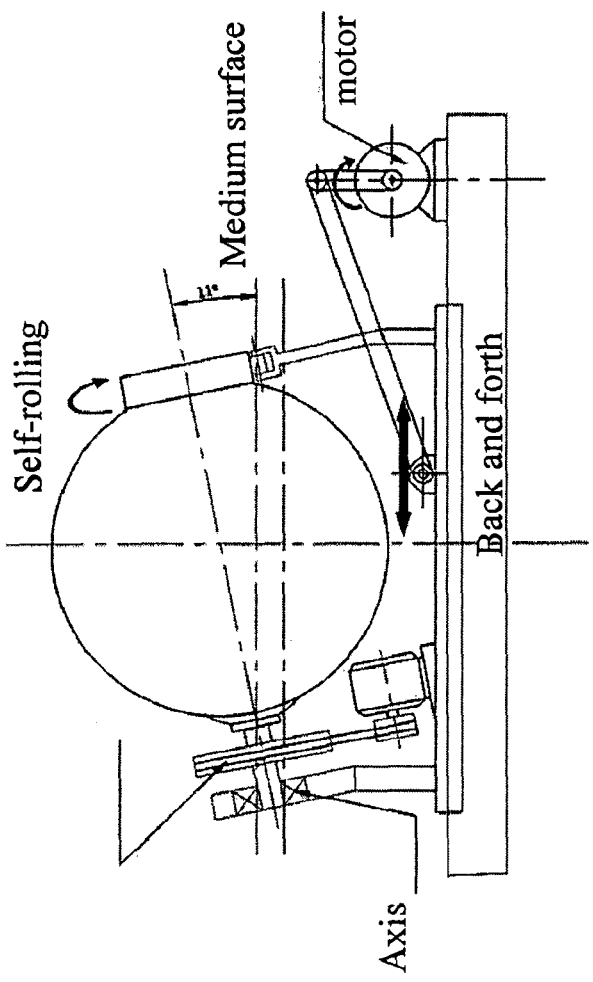
Figure 8a A ball-shaped self-rolling bioreactor with back and forth movement for culture medium mixing

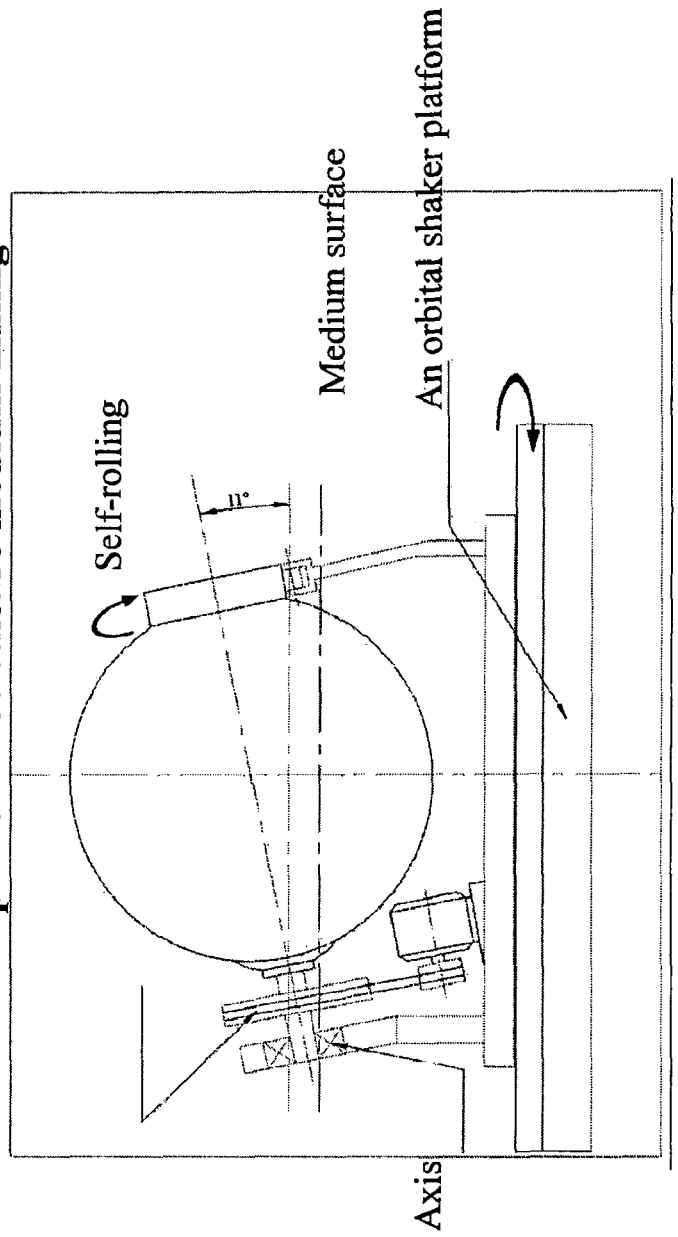
Figure 8b A ball-shaped self-rolling bioreactor on an orbital shaker platform for culture medium mixing

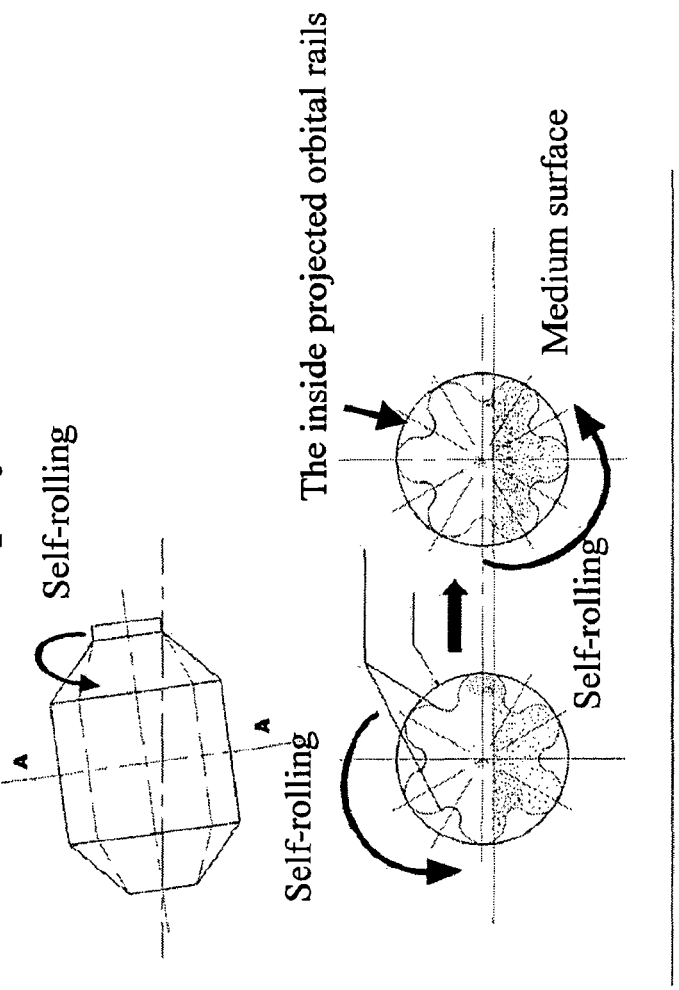
Figure 8c A cone-shaped self-rolling bioreactor vessel with inside projected orbital rails

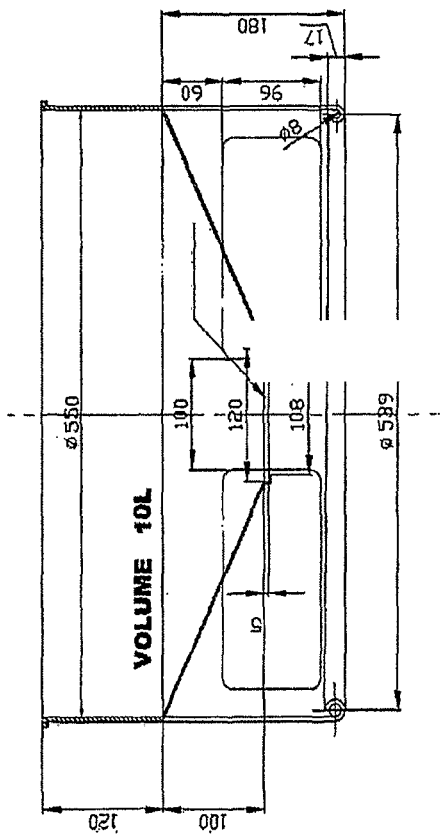
Figure 9a 10-liter vessel base with inverted frusto-conical bottom for plastic culture bag

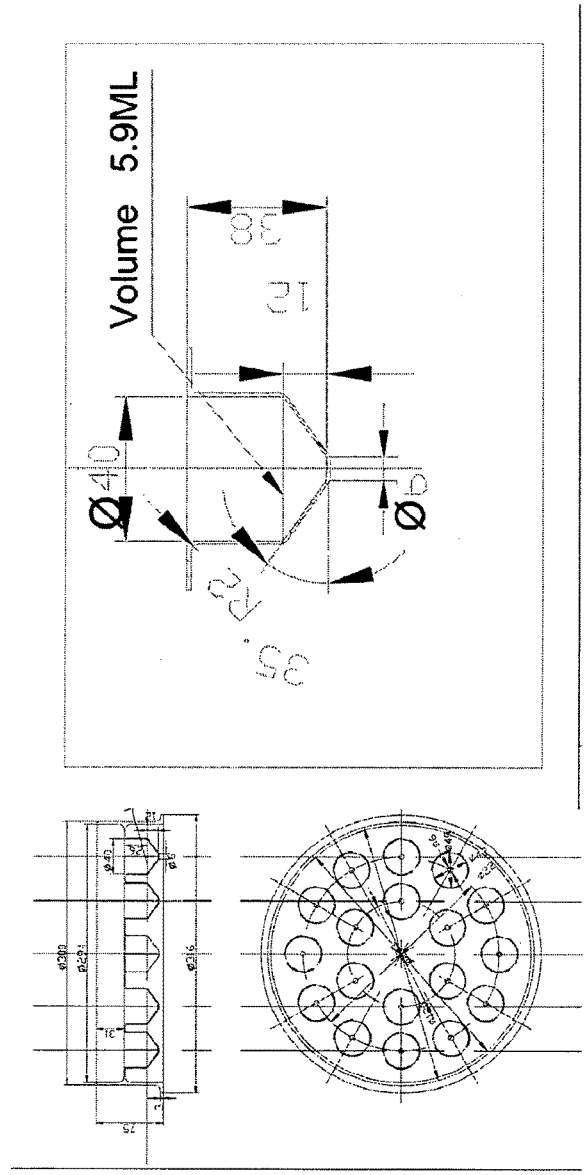
Figure 10b Shaker-based multiple wells with frusto-conical bottom for cell line robustness screening

METHOD TO INCREASE DISSOLVED OXYGEN IN A CULTURE VESSEL

CROSS-REFERENCE TO RELATED APPLICATIONS

This application is the National Stage of International Application No. PCT/US2006/037468, filed on Sep. 27, 2006, which claims the priority of International Application No. PCT/US2006/22312, filed on Jun. 8, 2006, the contents of both of the foregoing applications are hereby incorporated by reference in their entirety.

RELATED APPLICATION

This application is the continuation of patent application PCT/US06/22312 entitled "suspension culture vessels," filed on Jun. 8, 2006.

FIELD OF THE INVENTION

The present invention describes a method to make effective bioreactors.

BACKGROUND OF THE INVENTION

In our previous discovery described in a patent application PCT/US06/22312 entitled "suspension culture vessels," we had described a wide-body culture vessel with an inverted frusto-conical bottom on orbital shaker platform for suspension mammalian cell culture. Surprisingly, this system was significantly better than classical bioreactor and flat bottom shaker bottles. We had described this system making the culture medium climbing up onto the wall of the vessel easily with less hydro-mechanical stress. This system created a broad thin culture medium layer for extended surface, greater aeration and better mixing.

Interestingly, we did not know exact mechanism of action of this shaker-based frusto-conical bottom vessel system. In this invention, we have discovered the mechanism of action. Basing on the mechanism of action, namely a method to increase dissolved oxygen level in culture medium, we have designed and tested several types of mammalian cell culture bioreactors.

SUMMARY OF INVENTION

This invention describes mechanism of action of previously described suspension culture vessels with an inversed frusto-conical or inverted frustum bottom (patent application PCT/US06/22312). This invention discloses a method to increase dissolved oxygen (DO) in culture medium, which forms a foundation to design and make effective mammalian cell culture bioreactors.

BRIEF DESCRIPTION OF DRAWINGS

FIG. 1 A wide-body vessel with inverted frusto-conical bottom for suspension mammalian cell culture.

FIG. 3 150 ml work volume culture vessel with inverted frusto-conical bottom on shaker platform.

FIG. 8a A ball-shaped self-rolling bioreactor with back and forth movement for culture medium mixing.

FIG. 8b A ball-shaped self-rolling bioreactor on orbital shaker platform for culture medium mixing.

FIG. 8c A cone-shaped self-rolling bioreactor vessel with inside projected orbital rails.

FIG. 9a 10-liter vessel base with inverted frusto-conical bottom for plastic culture bag.

FIG. 9b 10-liter vessel base with inverted frusto-conical bottom.

FIG. 10b Shaker-based multiple wells with frusto-conical bottom for cell line robustness screening.

DETAILED DESCRIPTION OF THE INVENTION

This invention is based, at least in part, on the previous discovery that, without using sophisticated control tower and related DO and pH probes, suspension adapted mammalian cells grew significantly better in culture vessels with an inversed frusto-conical or inverted frustum bottom on a shaker platform with certain motion length than classical Applikon bioreactor as well as flat-bottom shaker bottles (FIG. 1).

Figure 2A:
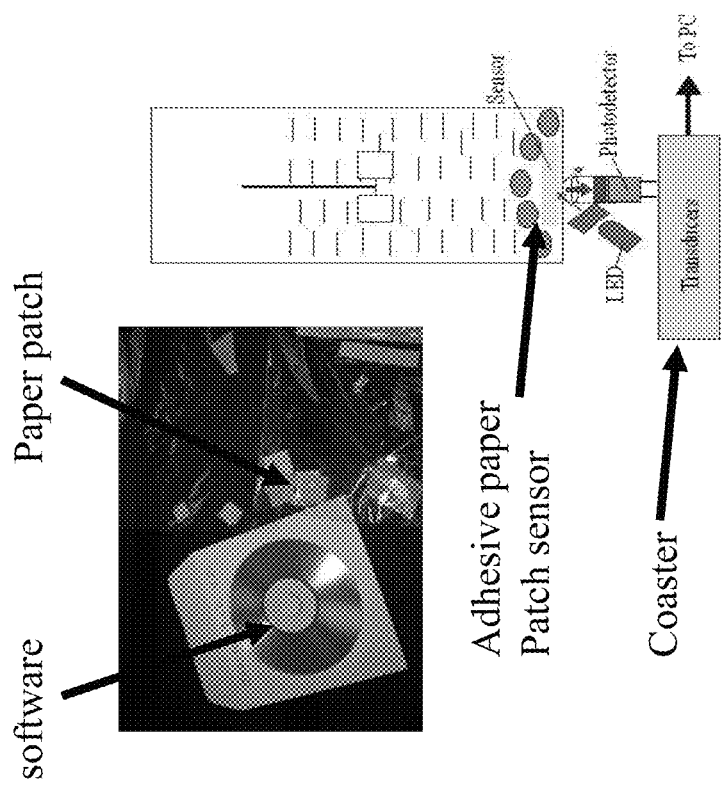
FIG. 2a Illustration of Flurometrix DO/pH patch sensor detection technology.

In order to study its mechanism of action, we have employed DO sensor, pH sensor and their detection system (Fluorometrix Corp., Stow, Mass.) (FIG. 2a,b). We have also employed a digital camera (Nikon) to catch and study detailed culture medium movement during shaking motion in the frusto-conical bottom vessels.

Figure 3:
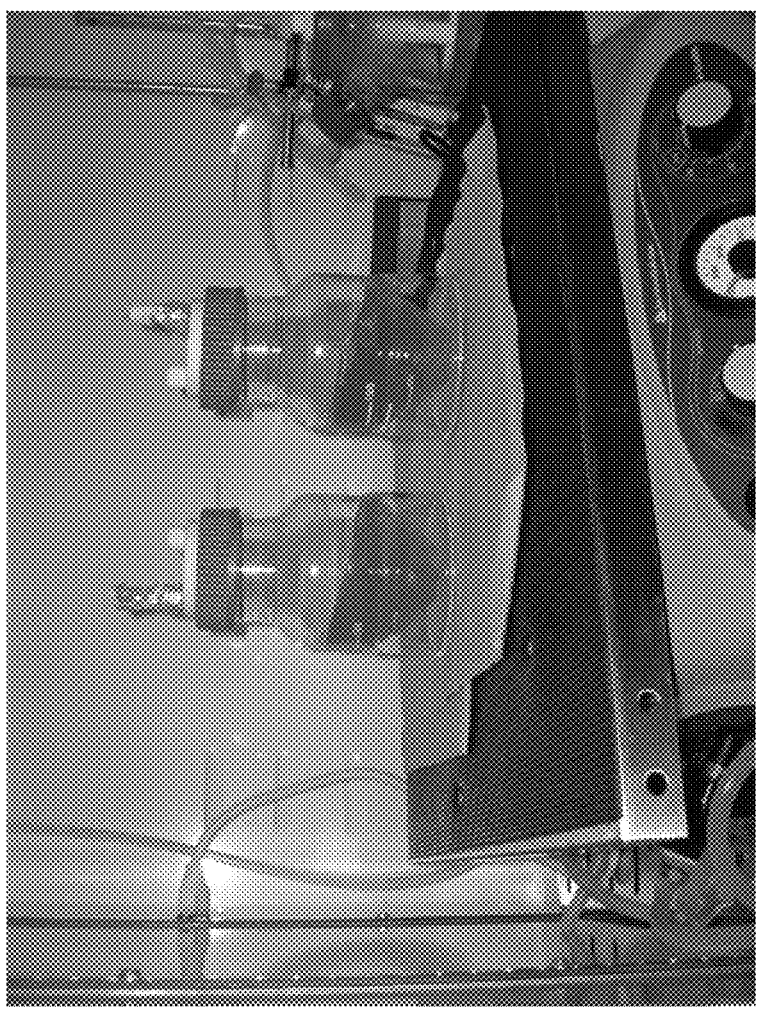
Figure 4:
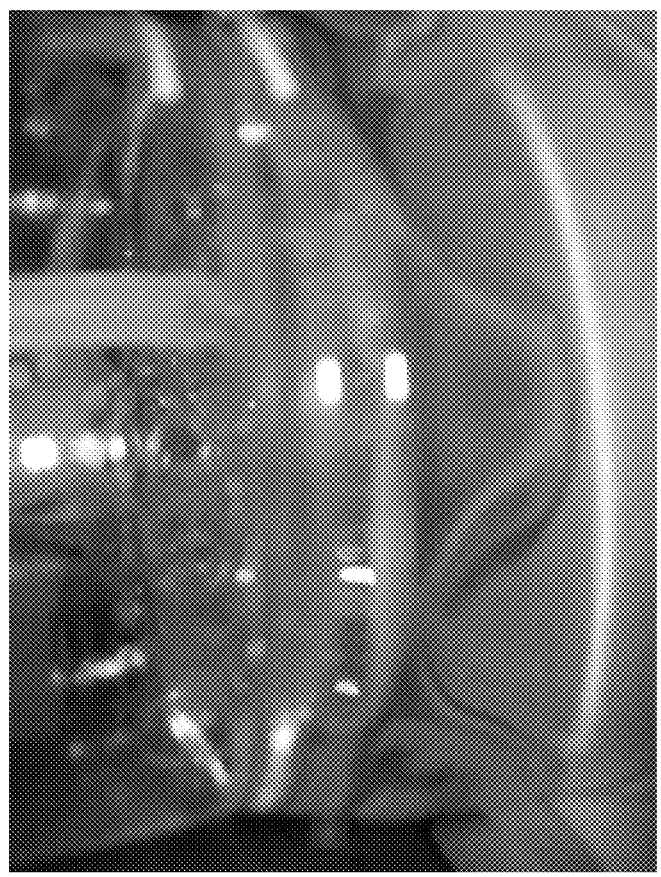
FIG. 4 Use of air pump to bubble the culture medium at static status to increase DO level.

First, we measured DO of the culture medium in 150 ml work volume vessel with inverted conical bottom (FIG. 3). We found that DO level easily reached 100% (Table 1). We then used air pump to bubble the culture medium in a same vessel at static status (FIG. 4). Surprising it was not able to reach 100% at a reasonable time period (Table 2). We were very surprised by this phenomenon since we routinely used air bubbling method to calibrate DO probe in 3-liter Applikon bioreactor and assumed that DO reached 100%. There must be a mechanism of action behind this phenomenon.

TABLE 1

Fresh culture medium was added in 150 ml work volume culture vessel with inverted frusto-conical bottom with shaking at 120 rpm (FIG. 3). Every 30 minutes, DO was measured.

| Time (min) | 0 | 30 | 30 | 30 |
|---|---|---|---|---|
| DO % | 45 | 75 | 92 | 100 |

TABLE 2

Fresh culture medium was added in 150 ml work volume culture vessel with inverted frusto-conical bottom without shaking. Air pump bubbling was used to add DO into the medium (FIG. 4). Every 30 minutes, DO was measured.

| Time (min) | 0 | 30 | 30 | 30 |
|---|---|---|---|---|
| DO % | 45 | 52 | 55 | 75 |

Figure 5A:
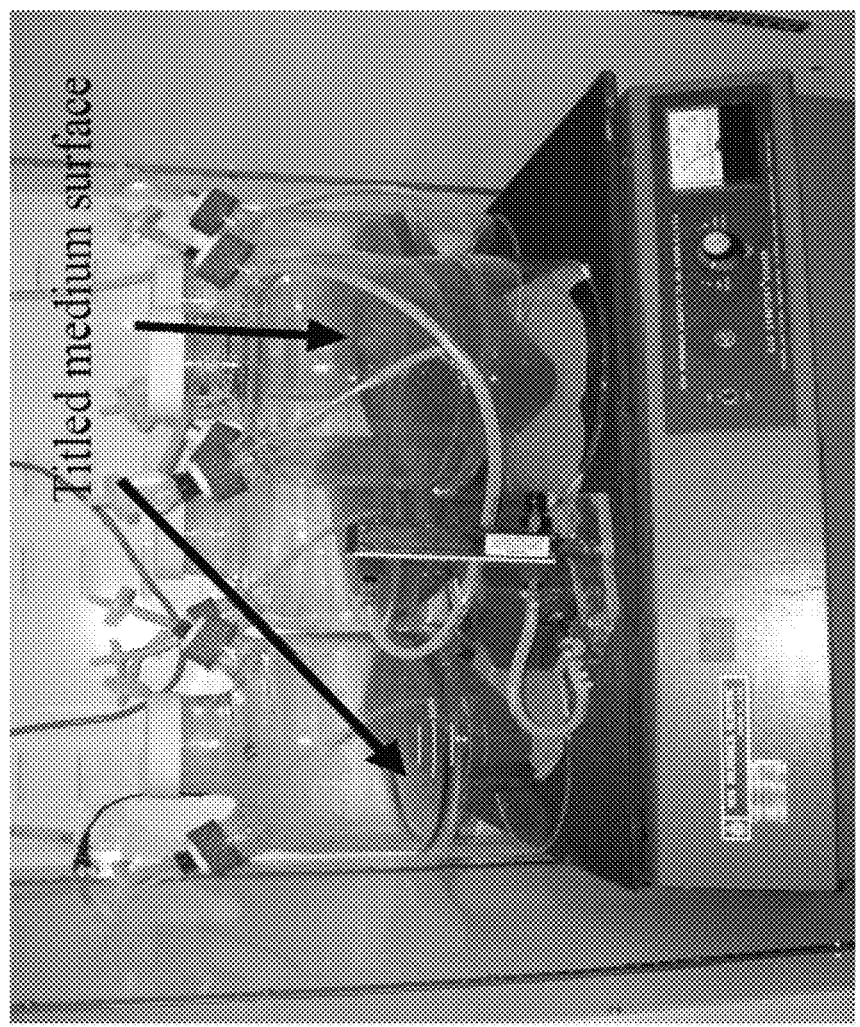
FIG. 5a, b, c, d, e Nikon digital camera captured instant medium surface characteristics. At an instant moment, all pictures showed tilted medium surface level mostly on one side of vessel wall (arrows). This characteristic of the medium movement increases DO in the culture medium by repetitively "sweeping" or washing air-exposed smooth vessel surface.
Figure 5B:
Figure 5C:
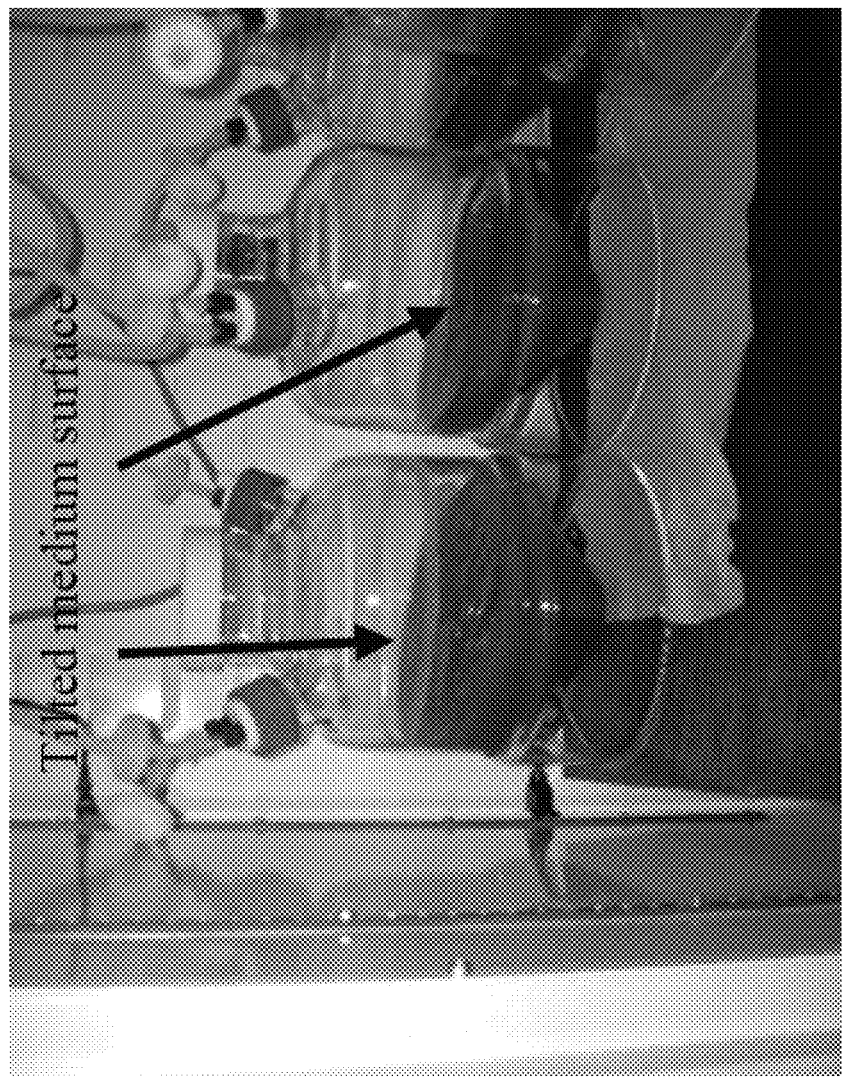
Figure 5D:
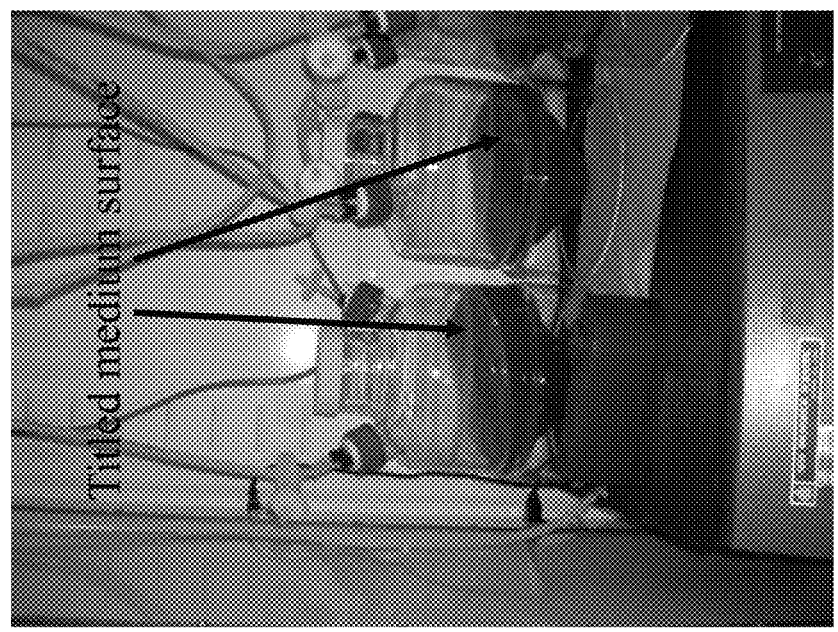

In search of the answer, we used high-speed camera to capture instant movement of the culture medium in the culture vessels with inverted frusto-conical bottom during the shaking (FIG. 5a, b, c, d)(FIG. 3). All the pictures clearly showed that at an instant moment, the culture medium is mostly on one side of culture vessels while most of other side is exposed to air contact. Due to the inverted conical bottom, shaking motion easily move the culture medium climbing onto the one side of vessels wall. This creates a circular movement of the medium current, repeatedly "sweeping" or washing the air exposed vessel wall. We hypothesized that this circular movement and its repetitive "sweeping" increased DO in the culture medium.

Dissolved oxygen (DO) is found in microscopic bubbles of oxygen that are mixed in the water or culture medium and occur between water molecules. In our case of the above, it is possible that tiny oxygen bubbles absorbed on the smooth glass or plastic surface and thus formed a microscopic layer of oxygen bubbles during the instant period of exposure to air. We then hypothesized that the instant formed air bubble layer on the smooth surface are so tiny which resembles the microscopic bubble size of DO in the water. This microscopic bubble layer is then "swept" or washed away by circulating medium current, thus making oxygen dissolved into water easily. This circular movement occurs again and again due to the frusto-conical bottom and shaking motion, thus increasing DO level more efficiently than direct air bubbling into the medium including sparging.

Figure 6A:
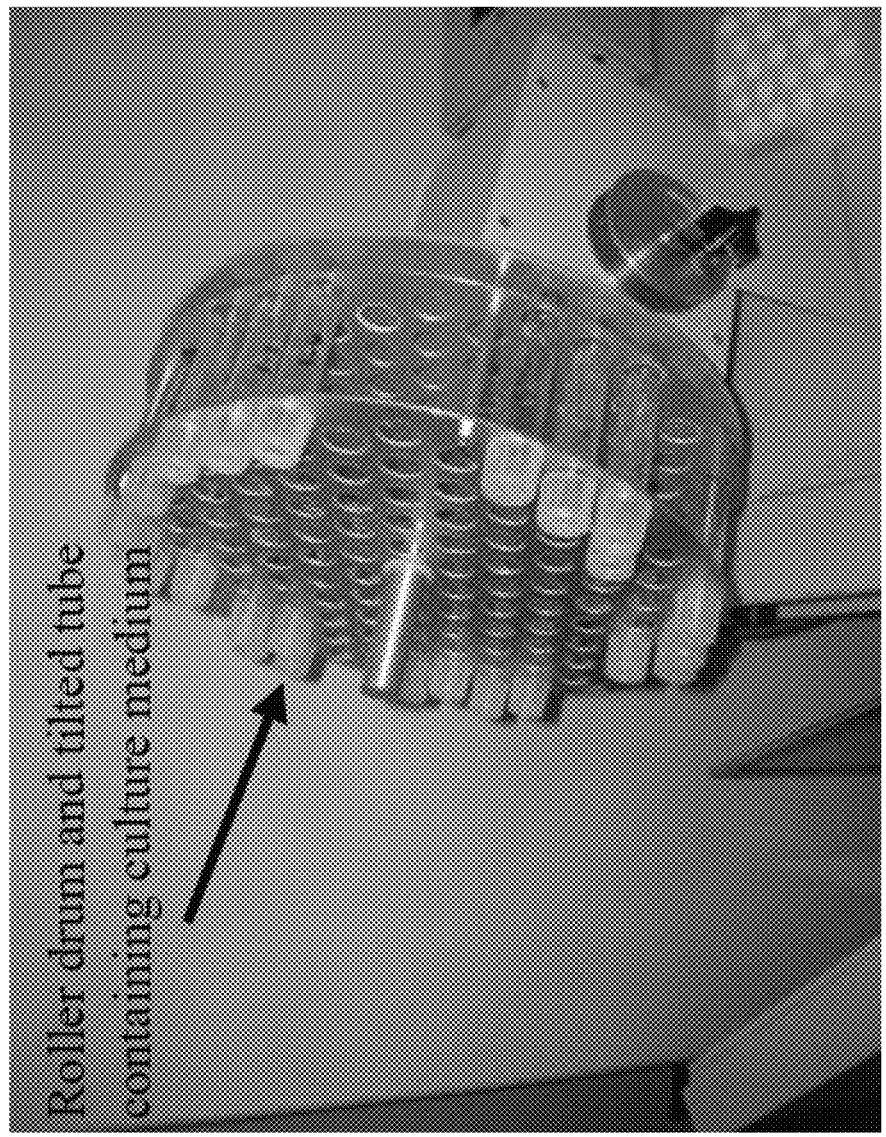
FIG. 6a, b Using rolling motion of titled plastic tubes, the culture medium inside the tube repetitively "sweeps" or washes the air-exposed smooth vessel wall surface. This movement increases DO in the medium rapidly to 100%.
Figure 6B:
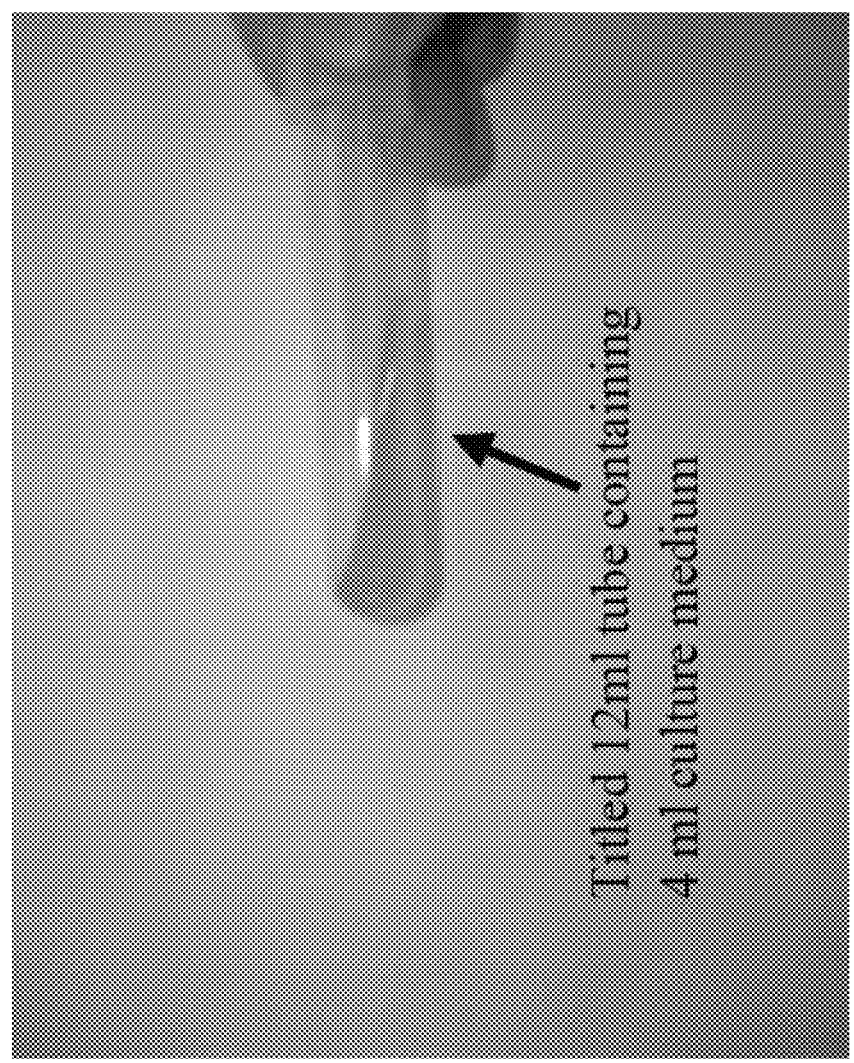

To test this hypothesis, we have employed 12 ml plastic tubes (NUNC) with 4 ml culture medium and roller drum at speed of 60 rpm (FIG. 6a, b). Shortly after 10 minutes of rolling, all the medium samples in the tubes have reached 100% DO. This study showed that culture medium or medium current repeatedly sweeping or contacting the air-exposed smooth surface with certain speed or force increased culture medium DO surprisingly effective.

Figure 7:
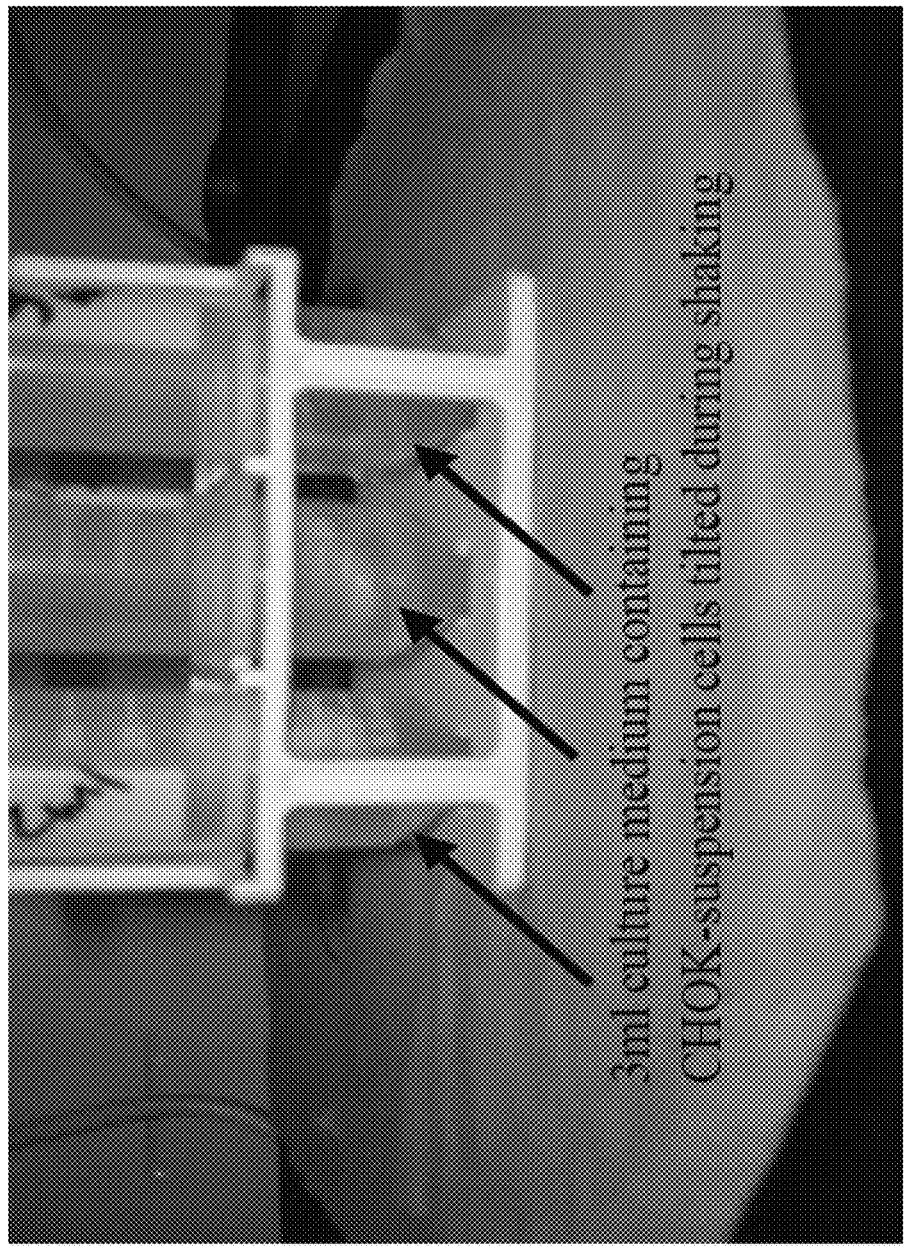
FIG. 7 Use of plastic tubes with inverted frusto-conical bottom (diameter 3 cm), suspension cultured CHOK cells easily reached 2.2% pcv in 4-days of culture on adjustable shaker platform with constant DO 100%. This created an effective mini-bioreactor system for cell clone robustness screening.

We then cultured CHOIR-suspension cells in the tubes on the roller drum at speed of 60 and 100 rpm for 4 days. As expected, DO have reached 100% in all the cases during these 4-day of culture. However, the cells did not grow at all. We thus concluded that there must be need for effective mixing besides of sufficient medium DO for optimal cell suspension cell culture. We then cultured the cells in 50 ml centrifuge tubes (NUNC) with inverted frusto-conical bottom on an adjustable shaker platform for 4 days (FIG. 7). All the cells grew and easily reached 2.2% packed cell volume (pcv). This result indicated that the mixing motion is required besides of sufficient DO for optimal suspension cell culture.

Basing on the above discoveries, we have designed several types of bioreactors for prototype construction. For each type, we have incorporated the method to increase DO in the culture medium by repeatedly using medium current to sweep or contact the air-exposed smooth surface with force together with sufficient medium mixing motion into consideration (FIG. 8a,b,c). Details are further described in Example-4.

We have also examined details of a batch-culture process by using a CHOK-suspension cell line expressing TNFR2-Fc-IL-1ra in a serum-free suspension culture medium. It was clearly shown that culture vessels with inverted frusto-conical bottom were ideal with optimal DO level, cell density, and yield of the product (Table 3). Details are also described in Example 1.

Example 1

Figure 2B:
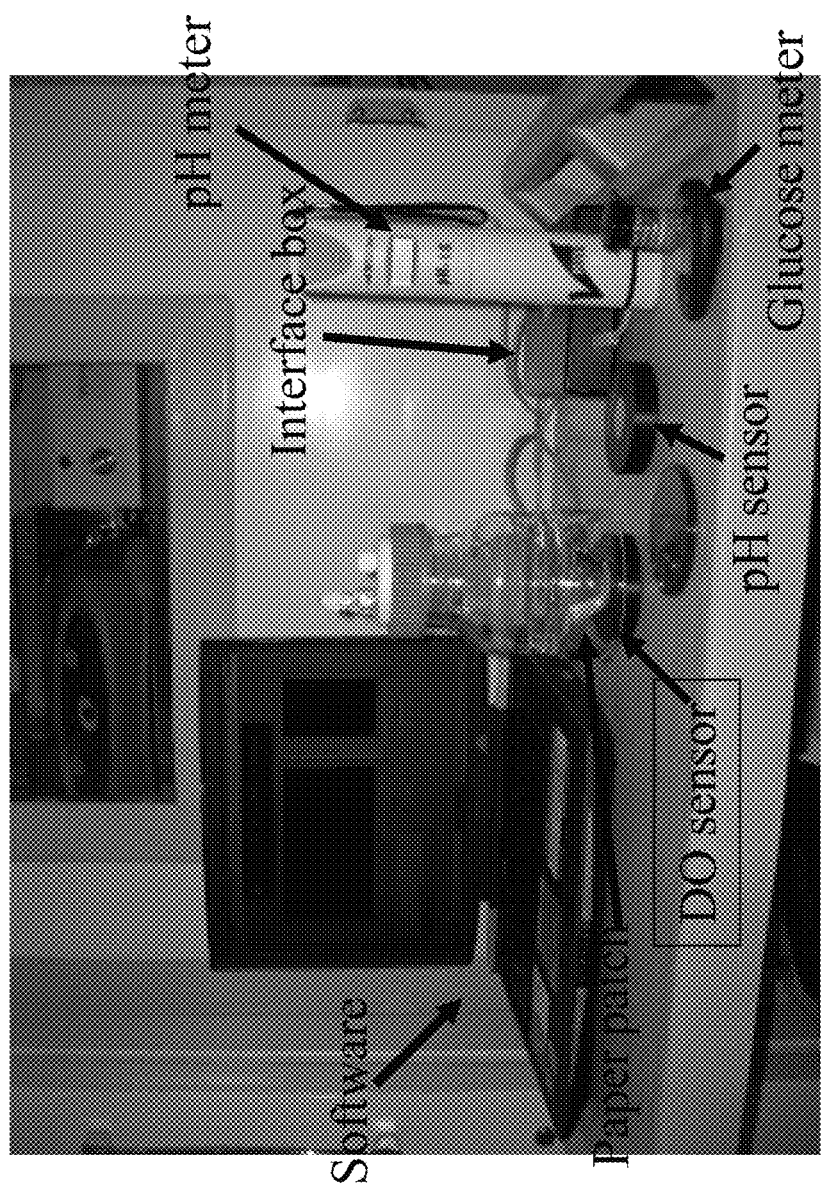
FIG. 2b Fluorometrix DO/pH patch sensor detection system.

Batch Culture Studying 150 ml Work Volume Vessel with Inverted Frusto-Conical Bottom Use of small-scale 150 ml work volume shaker vessels for batch culture of CHO production cell line expressing TNFR2-Fc-IL-1ra drug candidates was conducted in serum-free culture medium B001 for 8 days. DO was measured every day by using Flurometrix DO patch sensor detection system (FIG. 2a,b). Besides use of Flurometrix detection system, pH was also detected by a portable pH meter (FIG. 2b). Glucose was measured by a one-touch glucose meter (FIG. 2b). Table 3 clearly showed that culture vessels with inverted frusto-conical bottom were ideal with optimal DO level, cell density, and yield of the product.

TABLE 3

Simultaneously monitoring DO. pH, glucose. Mixing speed and temperature in a batch culture process in 150 ml work volume vessel with inverted frusto-conical bottom.

| | Day | | | | | | | |
|---|---|---|---|---|---|---|---|---|
| | 1 | 2 | 3 | 4 | 5 | 6 | 7 | 8 |
| DO % | 100 | 100 | 100 | 100 | 100 | 100 | 100 | 100 |
| pH | 7.5 | 7.4 | 7.0 | 6.8 | 6.6 | 6.6 | 6.7 | 6.8 |
| Glucose gram/L | 1.5 | 1.5 | 1.2 | 0.8 | 0.5 | 0.3 | 0.2 | 0.1 |
| Temperature | 37 | 37 | 37 | 34 | 34 | 34 | 34 | 34 |
| Mixing speed rpm | 120 | 120 | 120 | 120 | 120 | 120 | 120 | 120 |
| Expression titer mg/L | 22 | 55 | 115 | 220 | 415 | 530 | 705 | 750 |
| Cell density pcv % | 0.3% | 0.7% | 1.5% | 2.8% | 3.2% | 3.6% | 3.2% | 2.8% |

Example 2

Figure 9B:
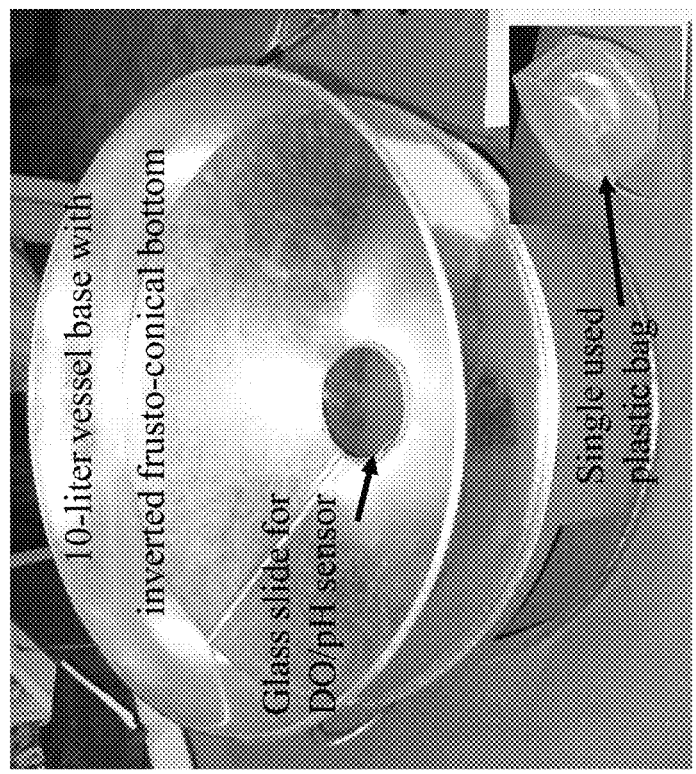

Making Single-Used Plastic Cell Culture Bags on Bioreactor Vessel Bases with Inverted Frusto-Conical Bottom Bioreactor vessel bases with inverted frusto-conical bottom and soft plastic bags (FIG. 9a, b) were designed and constructed. These bases and bags were designed to use in shaker platforms with adjustable motion length. The designed frusto-conical bottom together with adjustable shaker platform were intended to make the culture medium climbing as high as possible and as easier as possible (use of minimum shaking energy) to increase DO level in the medium and meet the challenge of high level use of O2 at high cell density culture condition. 3, 10, 20, 40, 100, 500 and 1000-liter size vessel bases and plastic bags have been designed for prototype construction and testing. Our goal is to construct cost-effective shear-force-less single-used mammalian culture bioreactors for R&D and industrial uses.

Example 3

Designing Shaker-Based Multiple Well Plate with Inverted Frusto-Conical Bottom for Production Clone Robustness Screening after High Throughput Protein Expression Titer Screening Robustness of a production cell line is important for stability of scale-up process and ultimate expression yield of a give protein drug. Among the high expression cell lines screened from thousands of cell clones, some of them are robust cell lines who meet industrial production cell standard. The selected robust cell lines are able to grow in high density for longer time and thus generate >10 fold higher expression titer than original screened cell clone expression titer.

Figure 10A:
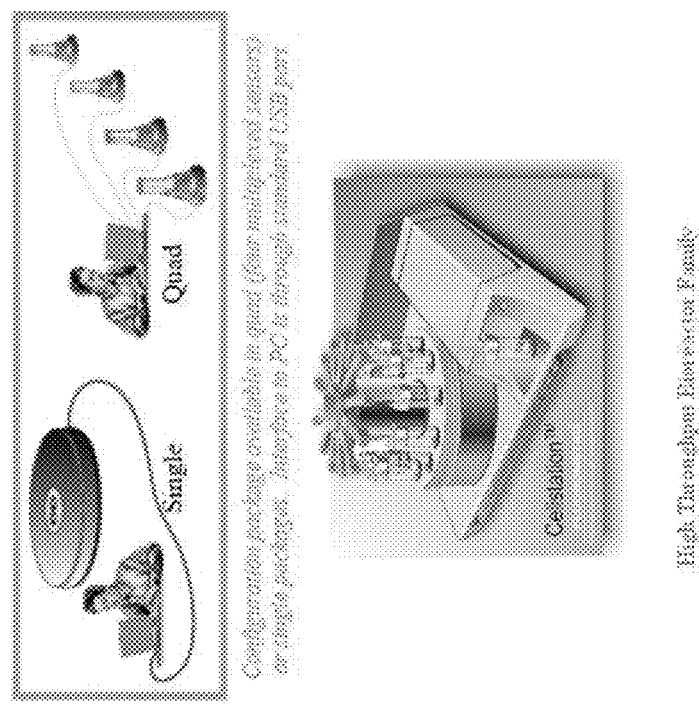
FIG. 10a current Flurometrix cell clone robustness screening and process optimization high-throughput mini-bioreactor system.

Current mini-bioreactor system (Fluorometrix Corp., Stow, Mass.) for cell line robustness screening and process optimization (FIG. 10a) is not optimized for high cell density cell growth and does not have optimal DO level to support of high density cell population. Thus it does not have screening of robust cell clones. Without sufficient medium DO, there is no way to optimize fed-batch process at high cell density.

The designed multiple well plate on shaker platform (FIG. 10b) will provide sufficient DO in the medium due to shaking motion and frusto-conical bottom of the culture wells to support high cell density growth, thus being able to screen a given cell line's ultimate capacity to grow in highest density and be distinguished from non-robust cell clones. This system is easy to handle and very cost-effective in addition.

Example 4

Design of Effective Bioreactors Basing on the Method to Increase DO in Culture Medium Combined with Effective Mixing Motion Basing on the above conducted roller drum experiments (FIG. 6a, b), we have discovered a method to increase DO in mammalian cell culture medium. We have then designed rolling bioreactors (FIG. 8a, b c). FIG. 8a shows a ball-shaped self-rolling bioreactor vessel by repetitively washing the air exposed vessel inner surface. This rolling movement increases DO in the culture medium to support high cell density growth. While a back and forth movement at ground level makes the culture medium well mixed during rolling movement (FIG. 8a). Together they support optimal suspension cell culture.

FIG. 8b shows an ball-shaped self-rolling bioreactor vessel. This rolling movement increases DO in the culture medium by repetitively washing the air exposed vessel inner surface to support high cell density growth. While an orbital shaker-platform at ground level makes the culture medium well mixed during rolling movement. Together they support optimal suspension cell culture.

FIG. 8c shows a cone-shaped self-rolling bioreactor vessel. This rolling movement increases DO in the culture medium by repetitively washing the air exposed vessel inner surface to support high cell density growth. While inside projected orbital rails make the culture medium move up to upper one end while rolling and fall back to the lower end. This additional movement helps culture medium mixing during rolling movement. Together they support optimal suspension cell culture.

The invention claimed is:

1. A method for oxygenating a culture medium comprising:
    providing a bioreactor system comprising a cell culture vessel, wherein said vessel comprises a cylindrical portion which has a diameter $\Phi 1$ and a height H1, and an inverted frusto-conical bottom which has a upper diameter $\Phi 2$, a height H2 and a bottom diameter of $\Phi 3$; wherein the cylindrical portion and the inverted frusto-conical bottom are connected and $\Phi 1=\Phi 2$; and wherein the diameters and heights of the vessel have the following relationship:
    $\Phi 1/H1=550/120$, and $\Phi 2/H2/\Phi 3=550/100/100$;
    introducing a culture medium into said vessel, wherein the vessel is at least partially filled with air; and
    moving the vessel by combining a circular movement with a motion selected from shaking, rocking, and back and forth movement, thereby enabling a circular movement of the medium current, repeatedly sweeping or washing the air exposed vessel wall, so that a microscopic layer of oxygen bubbles is formed on the vessel wall during the instant period of exposure to air and is swept or washed away by circulating medium current.

2. The method of claim 1, wherein the step of moving the vessel is conducted so that microscopic bubbles carrying oxygen molecules are generated and swept by the moving medium.

3. The method of claim 1, wherein moving the vessel is conducted repeatedly.

4. The method of claim 1, wherein the bioreactor system further comprises:
    a platform selected from: a moveable platform for moving the vessel back and forth, and an orbital shaker platform for moving the vessel in a circular motion; and
    a motor coupled to the platform for moving the culture vessel.

5. The method of claim 4, wherein microscopic bubbles carrying oxygen molecules are created in the medium by moving the vessel.

6. The method of claim 1, wherein the cell culture vessel has a volume of at least 3 liters.

* * * * *